United States Patent [19]

Sterzer

[11] Patent Number: 4,640,280

[45] Date of Patent: Feb. 3, 1987

[54] MICROWAVE HYPERTHERMIA WITH DIELECTRIC LENS FOCUSING

[75] Inventor: Fred Sterzer, Princeton, N.J.

[73] Assignee: RCA Corporation, Princeton, N.J.

[21] Appl. No.: 764,744

[22] Filed: Aug. 12, 1985

[51] Int. Cl.[4] ............................................. A61N 5/02
[52] U.S. Cl. ............................... 128/804; 219/10.55 F
[58] Field of Search ............... 128/804, 399, 660–663, 128/24 A; 219/10.55 R, 10.55 F; 350/418; 343/753, 909

[56] References Cited

U.S. PATENT DOCUMENTS

| | | | |
|---|---|---|---|
| 2,407,690 | 9/1946 | Southworth | 128/422 |
| 3,077,195 | 2/1963 | Folsche | 128/804 |
| 3,640,271 | 2/1972 | Horton | 128/662 |
| 4,140,130 | 2/1979 | Storm, III | 128/804 |
| 4,197,860 | 4/1980 | Sterzer | 128/804 |
| 4,282,887 | 8/1981 | Sterzer | 128/804 |
| 4,341,203 | 7/1982 | Bloxom | 126/440 |
| 4,532,939 | 8/1985 | Yukl | 128/804 |
| 4,556,070 | 12/1985 | Vaguine | 128/804 |

FOREIGN PATENT DOCUMENTS

| | | | |
|---|---|---|---|
| 2060923 | 7/1971 | Fed. Rep. of Germany | 343/753 |
| 2417263 | 10/1975 | Fed. Rep. of Germany | |
| 2508494 | 9/1976 | Fed. Rep. of Germany | 128/804 |
| 2648908 | 5/1978 | Fed. Rep. of Germany | 128/804 |
| S3855 | 4/1980 | Fed. Rep. of Germany | |
| 0028338 | 3/1977 | Japan | 350/418 |
| 0342419 | 2/1931 | United Kingdom | |
| 0431672 | 7/1935 | United Kingdom | |
| 0446660 | 5/1936 | United Kingdom | |
| 0502167 | 6/1937 | United Kingdom | |
| 0479735 | 7/1937 | United Kingdom | |
| 0762734 | 12/1956 | United Kingdom | |
| 0862646 | 3/1961 | United Kingdom | |

OTHER PUBLICATIONS

Article entitled: "Microwaves Score TKO in Flight Against Cancer", by: George Davis, published: Microwave Magazine, Oct. 1976, pp. 14 and 16.

Article entitled: "Determination of Power Absorption in Man Exposed to High Frequency Electromagnetic Fields by Thermographic Measurements on Scale Models", by: Guy et al., published in IEEE Transactions on Bromedical Engineering, vol. BME—23, No. 5, Sep. 1976.

Primary Examiner—Lee S. Cohen
Attorney, Agent, or Firm—Joseph S. Tripoli; Robert L. Troike; William H. Meise

[57] ABSTRACT

An arrangement for microwave or RF hyperthermia or for other microwave heating includes a source of microwave or RF radiation directed towards the substance to be heated. Interposed between the source and the substance is a lens in the shape of a portion of a cylinder or sphere. The lens has a dielectric constant greater than about 6 at the microwave or RF frequency to provide a focusing effect. The lens is located with the focus at the location to be heated. The lens can be solid or liquid-filled. The liquid can be deionized water.

5 Claims, 17 Drawing Figures

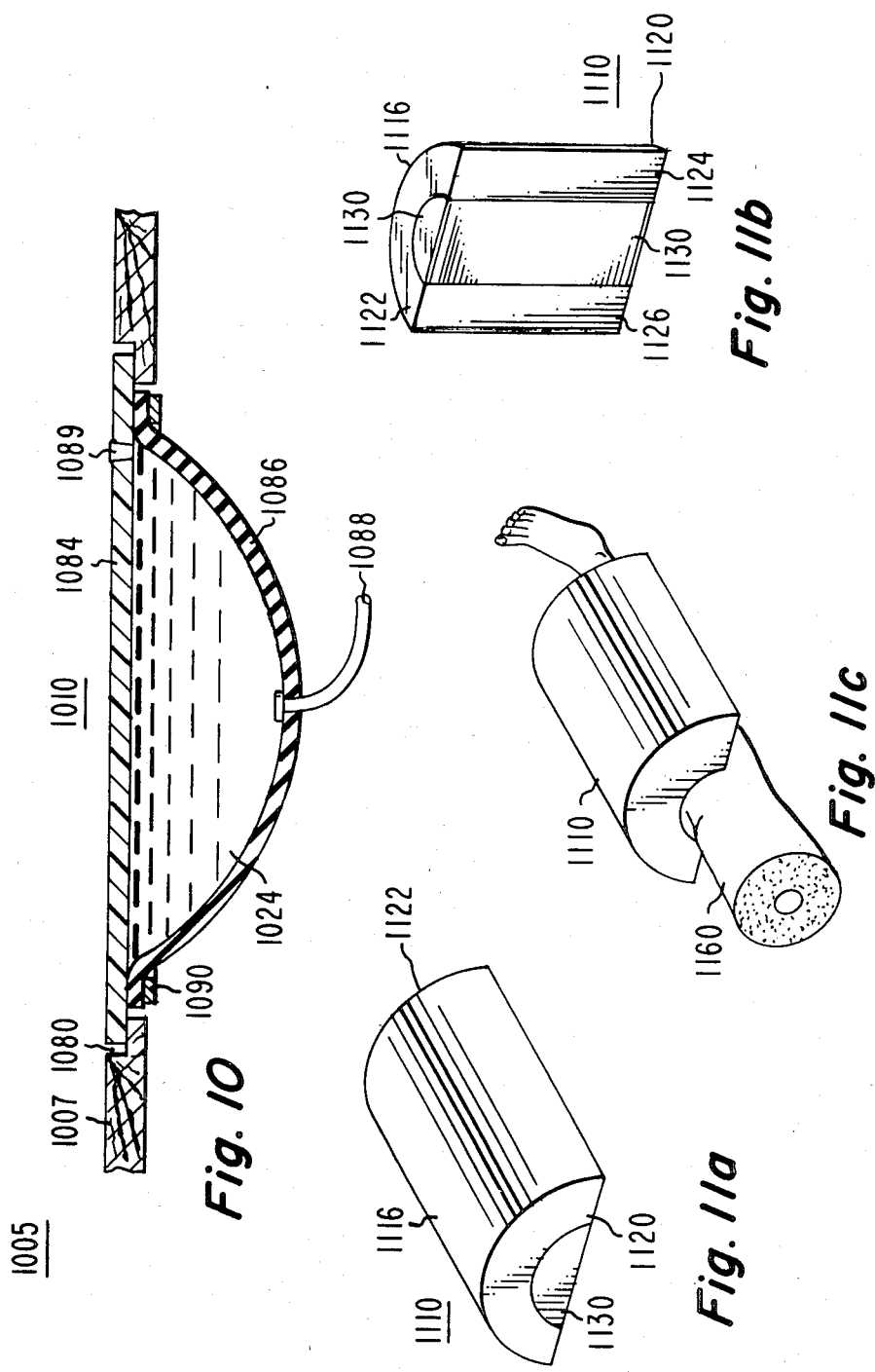

MICROWAVE HYPERTHERMIA WITH DIELECTRIC LENS FOCUSING

This invention relates to hyperthermia therapy in which the temperature of tissue in increased for therapeutic purposes, and particularly to the use of dielectric lens apparatus for focusing the heating effect at locations within the tissue being treated.

BACKGROUND OF THE INVENTION

Hyperthermia has been used for treatment of cancers for many years. It is known that raising temperatures of cells to above about 43° to 45° for sufficient time causes cell death and temperatures below about 41.5° generally do not affect the cells. Some types of malignant cells reportedly can be destroyed by raising their temperatures to levels slightly below those injurious to most normal cells. One of the techniques which has been used for hyperthermia is heating of the blood of a patient by an external apparatus, thereby raising the temperature of the entire body or of a portion thereof to the therapeutic temperature. This procedure risks substantial injury to the patient if temperature is not carefully controlled, and may fail to raise the temperature of the malignant cells sufficiently for destruction. Any malignant cells which remain undestroyed may cause a recurrence of the tumor, growth or malignance (hereinafter tumor).

Some surface tumors may be successfully treated by application of surface heat from a heated object. Deeply located tumors, however, are difficult to heat to therapeutic temperatures without destruction of the overlying tissue.

Another hyperthermia technique uses electromagnetic radiation to heat tissue. The electromagnetic radiation is often in the form of radio frequency (RF) or microwave radiation because of the ease of generating, controlling and directing microwaves, and also because of the absorption characteristics of tissue at microwave frequencies. At the current state of the art, electromagnetic hyperthermia is usually at frequencies in the range of 10 MHz to 6 GHz (herein termed radio frequency and microwave or RF&M). Radio frequency and microwave hyperthermia when applied to tissue containing a tumor generates heat within the tissue which raises the temperature of the tissue generally. It has been found that most tumors tend to have a limited blood supply by comparison with healthy tissue. Thus, the circulation of blood through a tumor is usually low by comparison with circulation through healthy tissue. At any electromagnetic power density, the tumor will usually be hotter than the surrounding healthy tissue because the more ample flow of blood in the healthy tissue provides cooling of the healthy tissue. Thus the tumor may be heated by RF&M hyperthermia to a therapeutic temperature without significant effect on the surrounding healthy tissue.

It has been found that RF&M hyperthermia when used in conjunction with either radiotherapy (ionizing radiation therapy) or with chemotherapy provides more consistent success that either alone. A course of treatment may include several radiotherapy treatments each week, interspersed with RF&M hyperthermia treatments. Widespread practical application of such combined therapy depends upon the availability of convenient and predictable RF&M hyperthermia method and apparatus.

U.S. Pat. No. 4,448,198 issued May 15, 1984, to Turner describes an invasive hyperthermia arrangement in which a plurality of microwave applicators are inserted into body tissue. The surgical implementation requires the use of an expensive operating room and the services of a skilled surgeon, which is not convenient. The applicators provide numerous potential sites for infection and at least require care by the patient. The implanted applicators may interfere with concurrent radiotherapy. Since the dielectric constant of the tumor may differ somewhat from that of the surrounding tissue, the energy from the microwave applicators may be partially reflected by the tumor if the applicators are implanted in healthy adjacent tissue, and this may result in an undesirable temperature distribution.

Noninvasive radio frequency and microwave hyperthermia relies upon heating from applicators placed outside the patient's body. This is particularly convenient for small surface tumors, the extent of which can be readily seen. The applicator is often held in contact with the surface being treated to avoid excessive spreading of the energy. The center of the applicator is directed towards the tumor, and the power is applied. Adjacent normal tissue is likely to be at a lower temperature than the temperature at the tumor because a simple applicator such as a horn has a power distribution which decreases away from the center or axis.

Tumors deep within tissue are more difficult to treat with radio frequency or microwaves, since the tissue overlying the tumor absorbs energy from the electromagnetic field entering the body. Thus, the electromagnetic field density at progressively deeper levels of the tissue progressively decreases. The increase in tissue temperature due to microwave heating tends to be a maximum at the surface of the tissue and to progressively decrease with increasing depth for uniform tissue heated by an applicator such as a horn antenna. Naturally, the actual amount of heating depends upon the relative absorption of the various different layers of tissue as a function of depth, the quantity and distribution of blood vessels available for cooling the various layers of tissue, and surface effects such as cooling of the skin by perspiration or air circulation.

A deeply located tumor can be heated to necrotic temperatures with an applicator such as a horn antenna, but this results in a power density at the surface of the skin sufficiently high to create burned areas. Burned areas subjected to radiotherapy tend to heal slowly or not at all. Ordinarily, radiotherapy is discontinued if the area to be irradiated is injured. Any burning of a part of a tumor or of the overlying tissue is therefore undesirable, as it limits therapeutic options. Thus, the treatment of deeply located tumors by noninvasive radio frequency or microwave techniques is difficult.

SUMMARY OF THE INVENTION

An apparatus for heating a location within a substance by means of radio frequency or microwave frequency electromagnetic radiation includes a source of radiation having a frequency or band of frequencies. Interposed between the source of microwave radiation and the substance to be heated is a radio frequency and microwave lens having a cross section in a shape of a portion of a circle. The lens is formed from a material which has a dielectric constant greater than about six at the frequency of the RF&M radiation. In a particular embodiment of the invention, the lens is in the shape of a portion of sphere. In another embodiment of the invention, the dielectric lens includes a dome shaped shell portion and a flat closure which together define a cavity, and the cavity is filled with liquid. In yet a further embodiment, a portion of the cavity enclosure is flexible.

DESCRIPTION OF THE DRAWING

FIGS. 10 and 11 illustrate other embodiments of the invention.

DESCRIPTION OF THE INVENTION

Figure 1:
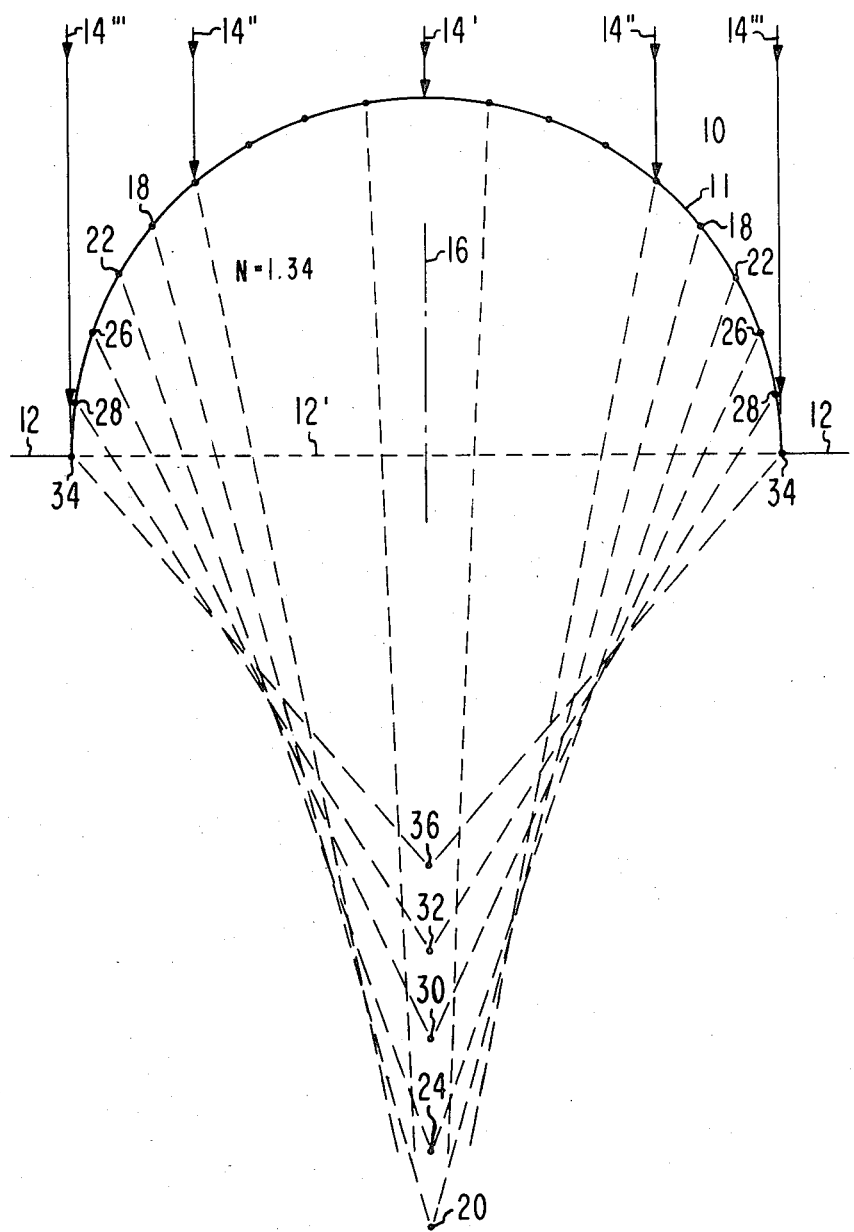
FIG. 1 is a representation of a hemispherical optical lens, illustrating ray paths aiding in understanding the line focus.

FIG. 1 illustrates a hemispheric form 10 raised above a surrounding flat area defined by a surface 12. Raised portion 10 and the region lying below surface 12 and its projection 12' are formed from the same material, which has an index of refraction (n) of 1.34. A plane electromagnetic wave illustrated by lines 14 falls from a source (not illustrated) upon surface 11 of hemisphere 10 parallel with axis of symmetry 16 of hemisphere 10. The ray paths near surface 11 may be determined and plotted by application of Snell's law $$\frac{\sin \alpha}{\sin \beta} = n$$

where $\alpha$ is the angle between the incident wave in air and a normal to the surface, and $\beta$ is the angle between the refracted ray in the dielectric medium and the normal to the surface. As illustrated by the dotted lines, that portion of the electromagnetic field represented by line 14' falling on the surface 11 of hemisphere 10 and near axis 16 of hemisphere 10 achieves a focus at such a large distance from surface 12 that the focal point is not shown. Electromagnetic energy represented by lines 14'' and 14''' falling on raised hemispheric portion 10 along a an annular locus or portion of hemisphere 10 passing through points 18 on the surface of hemisphere 10 is focused at a point 20. Electromagnetic energy falling on an annular locus passing through points 22 achieves a focus at a point 24, closer to surface 12 than point 20. Similarly, the electromagnetic energy falling on annular loci passing through points 26 and 28 achieve focuses (foci) at points 30 and 32, respectively. Energy intersecting hemispheric portion 10 tangentially at points 34 comes to a focus at a point 36, which is the closest focal point to projection 12' of surface 12. The index of refraction selected for FIG. 1 equals the index of refraction of water at light frequencies. Consequently, FIG. 1 may be considered to represent the focusing effect of a hemispheric bubble momentarily raised above surface 12 of an air/water interface. Alternatively, the bubble may be considered to be a solid hemisphere formed from a material of like dielectric constant such as paraffin or polyethylene. Those portions of light falling normally onto surface 12 are not refracted and are not focussed. In FIG. 1, the focusing effect of hemispheric bubble 10 is a line focus extending from infinity to point 36. Those portions of the radiation entering bubble 10 at points closer to axis 16 than points 18 achieve foci at distances from surface 12' greater than that of point 20. Energy entering precisely on axis 16 continues along the axis to an indefinite distance. The power represented by the light energy 14 falling on the surface of hemisphere 10 is therefore distributed along an extension of axis 16. The distance between points 20 and 36 in FIG. 1 is substantially equal to the radius of hemispheric lens 10. Thus, while there is a concentration of the energy, it is clear that if microwave radiation were substituted for light-frequency radiation, the arrangement illustrated in FIG. 1 would not be suitable for hyperthermia treatment because the line focus does not correspond to the shape of an ordinary tumor. A line focus of the sort illustrated in FIG. 1 might not have sufficient power density at the location of the tumor to cause necrosis, but might have a high enough power density at points on the line focus outside the tumor to cause damage to normal tissue.

Snell's law may be expressed as $$\sin \beta = \sin \alpha / n$$

This means that the maximum value which sin $\beta$ can take is unity, which occurs when $\alpha = 90°$, a grazing angle or ray tangent to the surface of the hemisphere. For an index of refraction of 6, the maximum value of sin $\beta$ is therefore 1/6, corresponding to a maximum angle $\beta$ of about 9.6°. This means that for a spherical lens having n=6 the maximum deviation of a refracted ray from the normal is 9.6°. Thus, all rays are essentially parallel to a normal to the spherical surface. Since a normal to the surface is also a radius, all rays are essentially at right angles to the hemispheric surface or essentially parallel to a radius, and converge upon the center of the sphere. The greater the index of refraction of the sphere, the closer the refracted rays are to parallelism with radii of the sphere.

Plots and analysis using Snell's law are based upon geometric optics, in which the assumption is made that a wavelength of radiation is much smaller than the lens structure. This condition applies to focusing of light. While not completely rigorous, Snell's law provides useful results in the analysis of focusing of radio frequency and microwave electromagnetic energy.

FIG. 2 illustrates lens arrangements similar to that of FIG. 1 for different indices of refraction. In FIG. 2a, hemispheric lens 210 raised above surface 212 has an index of refraction (n) of 1.5. Lens 210 has an axis of symmetry 216. Points 218 are on an annulus on the surface of lens 210 centered on axis 216. As illustrated, points 218 correspond to an angle 10° from the center of the hemisphere. Radio frequency or microwave electromagnetic energy falling at points 218 is focused by lens 210 at a point 219, while energy falling on lens 210 tangent to the surface at points 214 is focused at a point 215.

Foci are not illustrated for rays entering the surface of hemisphere 210 on axis 216 and in the region between axis 216 and annulus 218. For a uniform electromagnetic field falling upon hemisphere 210, only 3% of the field falls within the region bounded by annulus 218, and 97% falls on the remainder of the hemisphere and is focused on the line extending between points 215 and 219. Consequently, 97% of the energy falling on hemisphere 210 is focused on the line segment 215-219. The small amount of energy focussed from point 219 to infinity can be neglected.

Figure 2A:
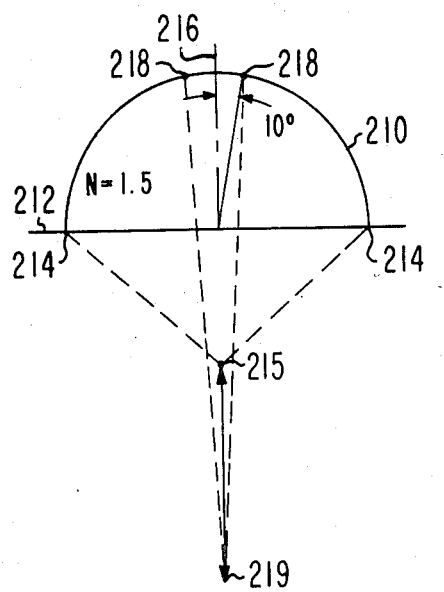
FIGS. 2a–2e are representations of hemispheric lenses having indices of refraction ranging from 1.5 to 6, illustrating the change in length and position of the line focus.
Figure 2B:
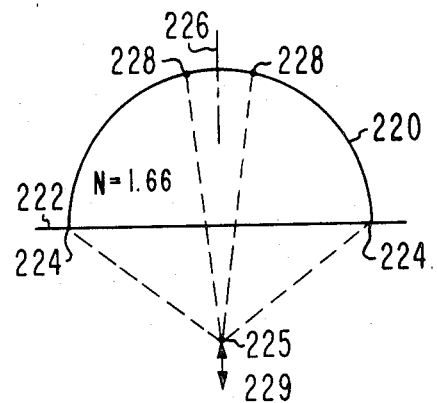

FIG. 2b illustrates a lens 220 formed above a surface 222. The index of refraction (n) of the material of lens 220 and underlying surface is 1.66. The RF&M energy falling on points defined by an annulus 228 lying 10° from an axis of symmetry 226 is focused at a point 229. Energy tangentially intersecting the surface of hemisphere 220 at points 224 is focused at a point 225. It can be seen that the length of the line focus between points 225 and 229 is much less than the length of the line focus between points 215 and 219 of FIG. 2a. This is attributable to the increase in the index of refraction.

Figure 2C:
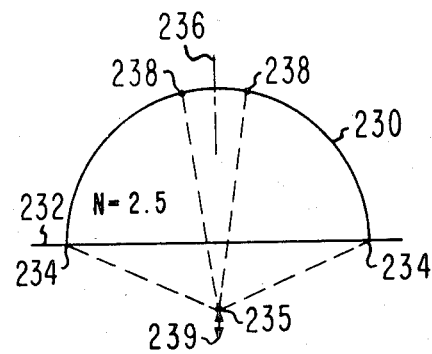
Figure 2D:
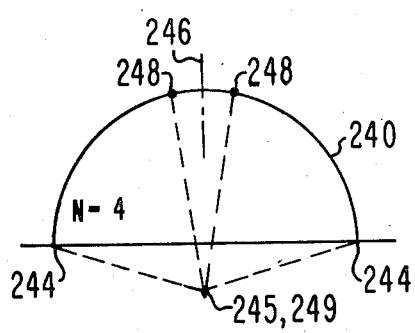
Figure 2E:
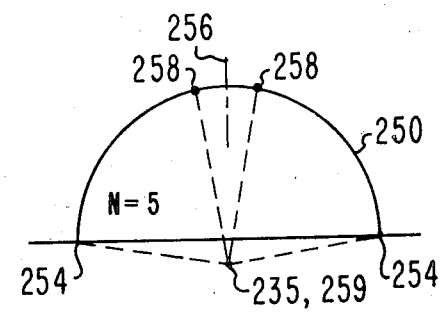

FIG. 2c corresponds to FIGS. 2a and 2b, but with n=2.5. The increase in the index of refraction results in the length of the line focus between points 235 and 239 being reduced by comparison with the arrangements of FIGS. 2a and 2b. FIGS. 2d and 2e show the line focus for indices of refraction of 4 and 6, respectively. It can be seen that the length of the line focus is essentially a point by comparison with the radius of the lens. Comparing FIGS. 2d and 2e, the focal point moves closer to the center of the sphere with increasing index of refraction. It is clear that line foci in which 97% of the energy is essentially focused at a point are suitable for hyperthermia. Thus, the arrangements of FIGS. 2d and 2e having indices of refraction of 4 and 6, respectively, produce essentially point foci and are eminently suitable for hyperthermia. The energy distribution along focal line 235-239 of FIG. 2c is satisfactory for some purposes, and therefore an index of refraction of 2.5 is also satisfactory. Relatively longer line foci will tend to distribute the energy received by the lens over too long a path for most practical applications, and are therefore not useful. The relationship of relative dielectric constant ($\epsilon_r$) to index of refraction (n) is given by the equation.

$$\epsilon_r = n^2$$

An index of refraction of 2.5 corresponds to a dielectric constant of about 6. For purposes of comparison, the dielectric constant of water is about 1.8 (n=1.34) at optical frequencies and about 79 (n=8.9) at microwave frequencies.

Figure 3A:
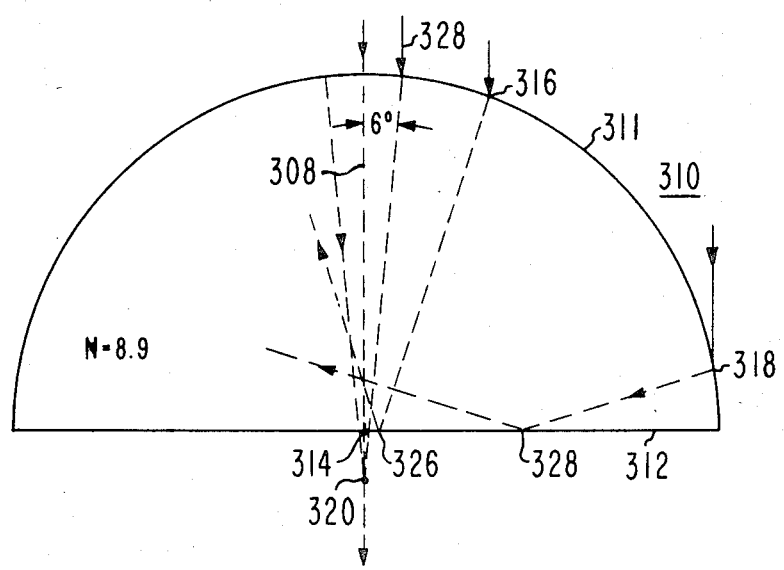
FIG. 3a illustrates a hemispheric lens formed from a material having an index of refraction near 9 completely surrounded by air, with ray paths illustrating total internal reflection.

FIG. 3a illustrates a hemispheric lens 310 having a domed hemispheric surface 311 and a flat surface 312 passing diametrically through the center 314. The index of refraction of lens 310 is 8.9, corresponding to the index of refraction water at microwave frequencies.

Lens 310 is completely surrounded by air having an index of refraction of approximately unity. As illustrated, RF&M energy entering surface 311 at points 316 and 318 and travelling towards focal point 320 is totally internally reflected at points 326 and 328, respectively, and is dissipated in the internal losses of the lens. Only energy entering lens 300 within a small region around axis of symmetry 308 passes through bottom surface 312. For example, ray 328 entering about 6° away from central axis 308 is not reflected at surface 312, but instead passes through surface 312. Only about 1% of the total energy entering surface 311 exits from surface 312. The energy entering lens 300 within the approximate 6° cone as illustrated is not focused at point 320 but instead is widely deflected as it leaves surface 312.

Figure 3B:
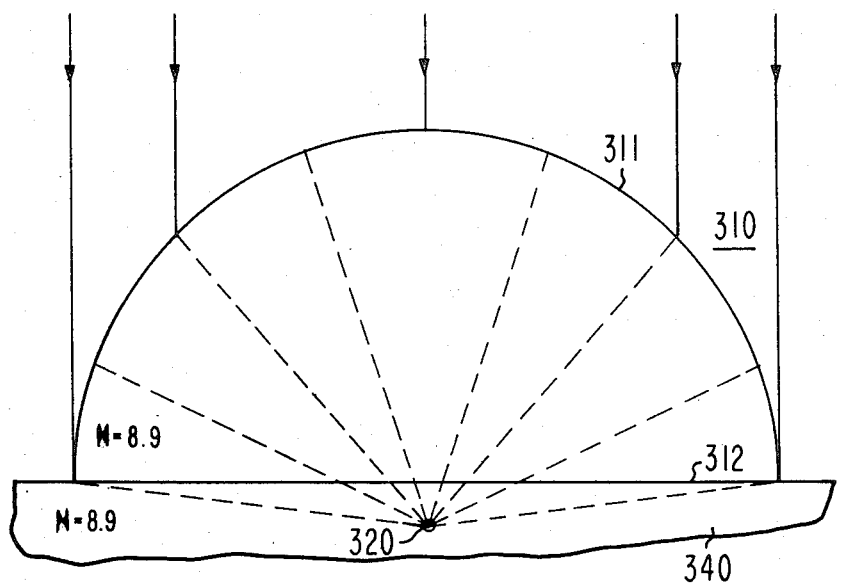
FIG. 3b illustrates the same lens overlying a substance to be heated, also having an index of refraction near 9, showing focus of the energy at a focal point within the substance.

FIG. 3b illustrates the same hemispheric lens 310 having an index of refraction of 8.9, but with bottom surface 312 in contact with a substance to be heated which is designated as 340. Substance 340 has the same dielectric constant as lens 310. With the situation illustrated in FIG. 3b, the microwave energy passes through the lower surface 312 of lens 300 and into substance 340 without any discontinuity or internal reflection. The focal point, as illustrated, is beneath the surface of substance 340 at a point 320. The energy entering substance 340 at the interface with surface 312 is distributed over the entire surface under the hemispheric lens. This keeps the electromagnetic field density low at the surface and tends to keep the temperatures at the surface of the substance relatively low. The power density at the focal point is high, and tends to raise the temperature at the focal point above that of the surrounding substance. In a particularly advantageous embodiment of the invention suitable for hyperthermia use, lens 310 is water filled to provide a dielectric constant of 8.9, which approximately corresponds to the dielectric constant of human tissues, which are largely composed of water.

Figure 4:
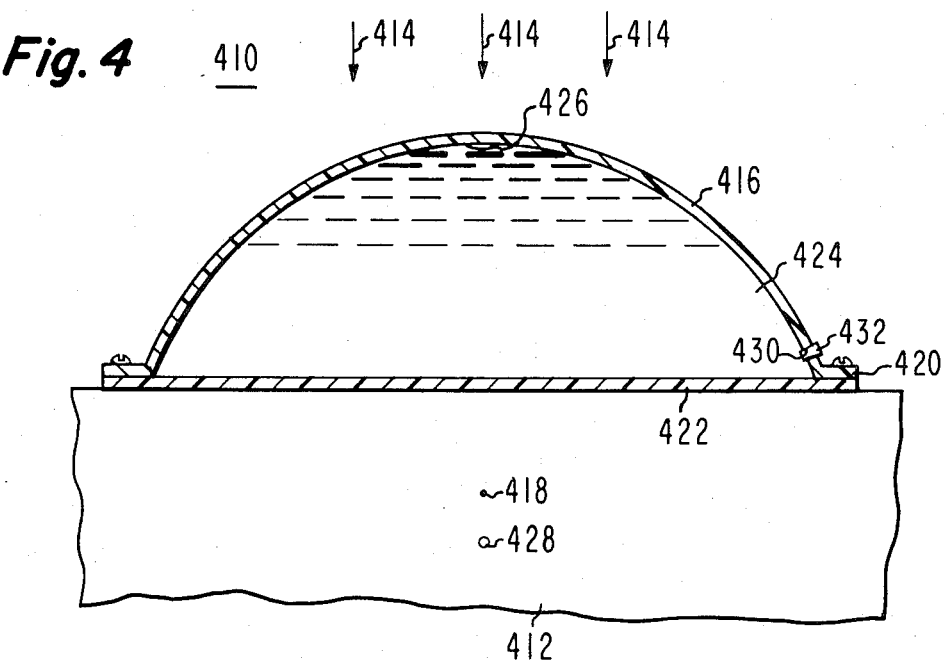
FIG. 4 illustrates a hyperthermia arrangement according to the invention, including a cross-sectional view of water-filled semispheric lens.

FIG. 4 illustrates a hyperthermia arrangement according to the invention. In FIG. 4, radio frequency or microwave radiation illustrated by lines 414 falls onto a lens 410 overlying a portion 412 of tissue which is part of a patient being treated. Lens 410 includes a dome-shaped plastic shell 416 having a center of curvature at a point 418 which lies within tissue portion 412. A flange 420 which is part of shell 416 is affixed by screws and sealant to a flat plastic plate 422. Shell 416 and plate 422 when assembled in this fashion define a cavity 424 in the shape of a portion of a sphere. It should be noted that cavity 424 does not define a hemisphere. It is a portion of a sphere which is termed a semisphere (the term may also include a portion of a sphere greater than a hemisphere). The focal point of semispherical lens 410 is at a point 428 within tissue portion 412. Cavity 424 is filled with water as illustrated, except for a small bubble 426 located on the inside of shell 416 at the top of cavity 424. Bubble 426 is small and causes only a minor perturbation of the spherical shape of the water contained within shell 416. It should be noted that ordinary plastic materials such as polyethylene or methacrylic resin (plexiglass) which might be used for the shell have indices of refraction (in the vicinity of 1.5) which are much less than the index of refraction of water (about 9 at microwave frequencies), and consequently the lens cannot properly be said to include shell 416 and plate 422. Naturally, it is possible to make the shell and plate from materials having a greater index of refraction, but this is not necessary.

Access to cavity 424 for purposes of filling and emptying the lens is obtained by a hole 430 located along one edge of dome 416 which is closed by a synthetic rubber stopper illustrated as 432.

Ordinary tap water is unsatisfactory as a filling material for lens 410, because of its excessive energy absorption or loss at RF&M frequencies. The excessive loss of tap water reduces the efficiency of lens 410 by causing absorption of the electromagnetic energy in preference to transmission of the energy to focal point 428. This in turn disadvantageously causes heating of the water, as described below.

In order to use lens 410 for hyperthermia, lens 410 is turned on its side and filled with deionized water, which is readily available in most hospitals. The stopper is replaced and the lens is placed over the portion of the patient to be treated. The flat plate 422 of lens 410 is pressed against a surface of the tissue portion to be treated in order to reduce the size of any voids between the tissue and the lens. As described above, such voids can cause total internal reflection of the microwave energy within the lens water, which reduces the energy available for therapeutic purposes. Straps (not illustrated) may be used to hold the lens firmly in place. With lens 410 in position, RF&M energy is applied from an antenna (not illustrated in FIG. 4) directed towards the lens and the patient. The energy is applied for a length of time sufficient to raise the tumor being treated to the desired temperature. The temperature is measured by known invasive or noninvasive techniques.

During treatment, the energy focused on point 428 enters tissue 412 over a relatively large surface area, as mentioned above. Consequently, the power density at any point on the tissue surface is relatively low. A low power density at the tissue surface tends to reduce the amount of temperature rise of tissues overlying the location of focal point 428 at which the tumor is located. As also mentioned previously, all of the overlying tissues absorb power from the electromagnetic field. Thus, notwithstanding that the power density at the surface of tissue 412 is low by reason of the distribution of the energy over a large area, there may nevertheless be a substantial temperature rise due to the fact that the energy at the surface of tissue 412 facing lens 410 is not attenuated by intervening layers of lossy tissue. The arrangement of FIG. 4 aids in cooling the surface layers of tissue of 412. Heat from the surface layers of tissue 412 facing lens 410 flows through plate 422 into the relatively cold water filling cavity 424.

Figure 5:
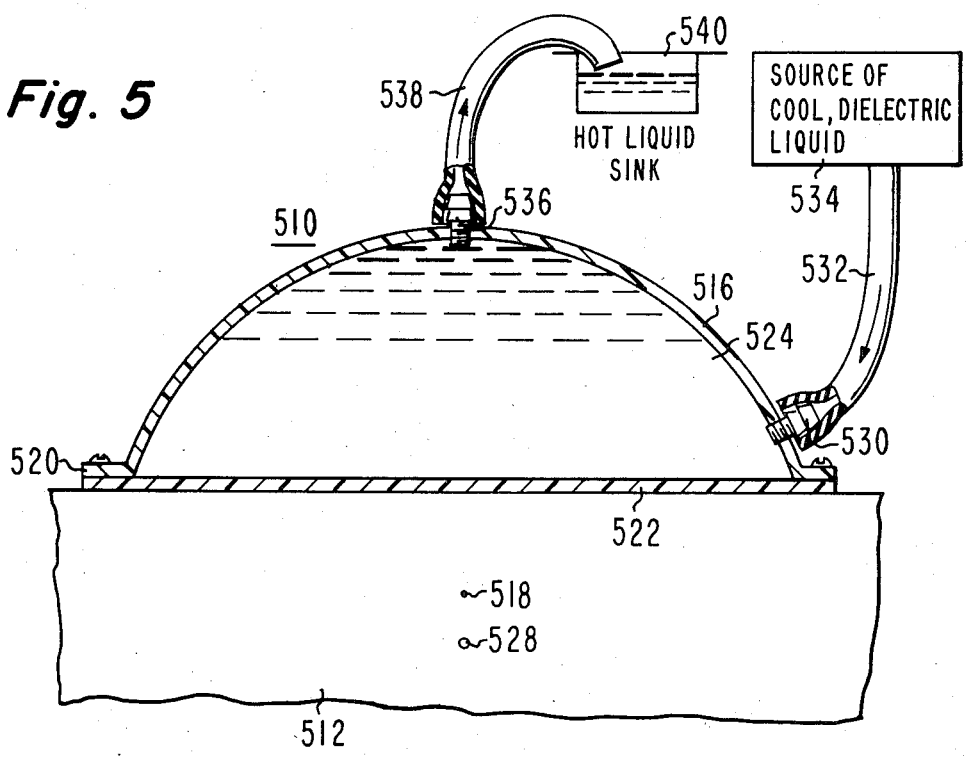
FIG. 5 illustrates a hyperthermia arrangement similar to that of FIG. 4, including an arrangement for cooling the lens liquid.

The water in cavity 424 will tend to become warmer during the hyperthermia treatment. The water absorbs heat from tissue portion 412 through plate 422, and also directly absorbs energy from the microwave field due to the finite loss of the water. FIG. 5 illustrates an arrangement similar to that of FIG. 4 which includes tubes by which cool water can be introduced into the cavity and warm water removed so as to aid in maintaining the temperature of surface portions of tissue 412 adjacent lens 410 below levels injurious to tissue.

In FIG. 5, a lens designated generally as 510 includes a rigid thermoplastic domed shell 516 and flange 520 assembled to a rigid disk 522 to form a semispheric cavity 524 which is filled with water, generally as in FIG. 4. Since cooling of the surface of tissue 512 adjacent plate 522 occurs by heat transfer through plate 522, it is desirable to have cooled water adjacent plate 522. In the arrangement of FIG. 5, a hose connection fitting 530 threaded through rigid shell 516 is connected by means of a clamp (not illustrated) to hose 532 which is connected to a source 534 of cooled dielectric liquid. Source 534 may be, for example, a large tank of cool liquid. Liquid flows from source 534 through hose 532 under relatively low pressure so as to generate a flow which enters cavity 524 of lens 510 with a low velocity, so as not to create turbulence. The relatively cool liquid entering through fitting 530 settles to the bottom of cavity 524 and lies against plate 522 because of its greater density by comparison with warmer overlying liquid. As the liquid against plate 522 is warmed by conduction and by direct microwave heating, it rises towards the top of the domed cavity and is replaced by a fresh flow of cool liquid. At the top of lens 510, a second hose fitting 536 threaded through domed shell 516 provides an egress for the warmest liquid, which flows through a hose illustrated as 538 to a sink 540 for the hot liquid. Hot liquid from the sink may be cooled and recirculated to source 534 for reuse as by a closed refrigeration unit.

The lenses so far described have rigid outer peripheries or shells. The focal point is at a substantially fixed location relative to the flat side of the lens. If the location of the tumor is at a greater distance from the surface of the tissues to be treated than the focal point is from the flat surface, the hyperthermia apparatus may heat a location between the surface of the tissue and the tumor to a higher temperature than the tumor itself. Generally, simply pressing the lens against the overlying flesh is not fully effective in collocating the focal point and a deep tumor, because pressure on the overlying tissue also pushes the deep seated tumor away. Pressure is also not useful to collocate the focal point and the tumor when a bony structure such as the cranium intervenes. Furthermore, a problem arises when the tumor is located at a distance from the surface of the tissues to be treated which is less than the distance of the focal point of the lens from the flat surface. In this arrangement, heating of the tumor requires that the flat surface of the lens be spaced away from the surface of the tissues. This introduces a large air space between the lens and the tissues. The large air space will tend to cause internal reflections in the lens which reduce the amount of microwave energy coupled into the tissues. In order to have a variety of spacings between the focal point of a lens and the surface of the lens facing the patient, it may be desirable for a hospital or treatment center to have on hand a number of hemispherical lenses made from different materials. The lens having the appropriate focal point is selected for each application.

Figure 6:
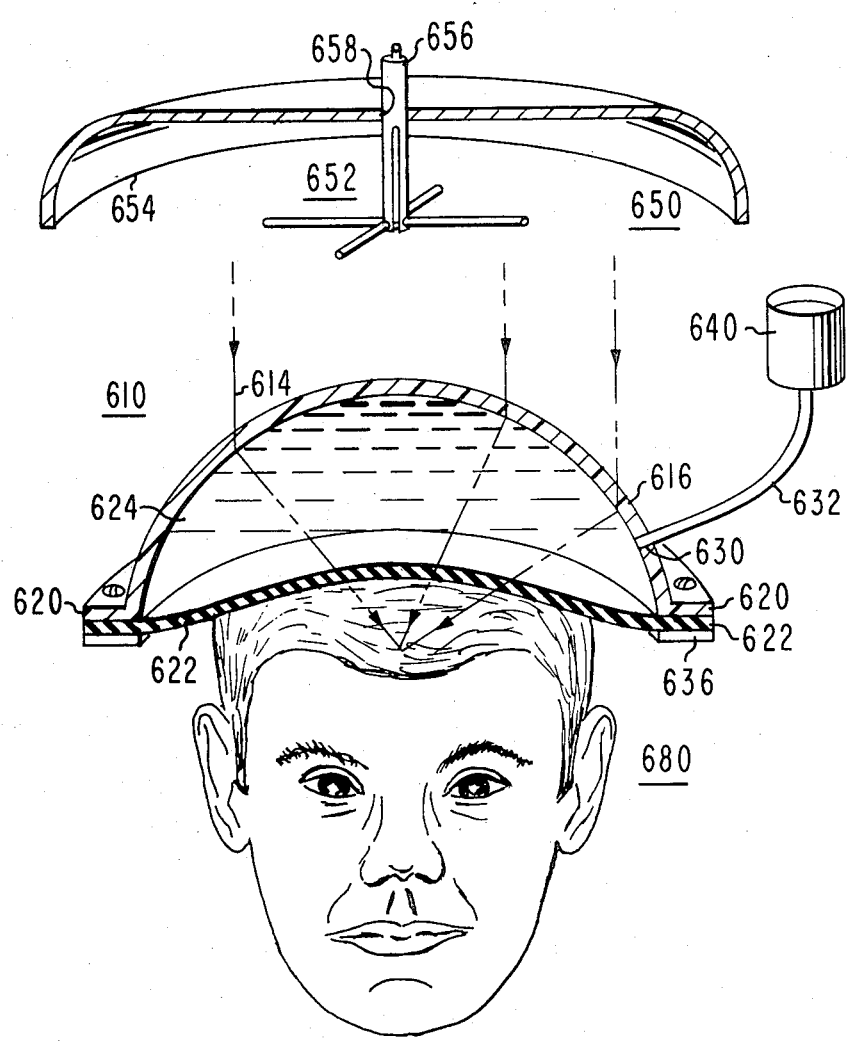
FIG. 6 illustrates a hyperthermia arrangement having an antenna and a lens, in which a portion of the lens defining shell is elastic rather than rigid, thereby allowing adjustment of the position of the lens relative to the tumor.

FIG. 6 illustrates a hyperthermia arrangement in which good coupling is maintain between the lens and the surface of the tissue overlying a tumor notwithstanding variations in the distance of the tumor from the surface of the overlying tissue. In FIG. 6, a water filled lens 610 is located between an antenna designated generally as 650 and the head designated generally as 680 of a person undergoing hyperthermia treatment. Lens 610 includes a rigid thermoplastic shell 616 having a circular flange 620. A thin plastic or rubber membrane or diaphragm 622 is stretched about the periphery of the cavity 624 defined by shell 616. Membrane 622 is clamped to flange 620 by a ring 636 which is itself clamped to flange 620 by a plurality of screws, only two of which are shown. The joint between membrane 622 and flange 620 is made fluid-tight by a sealant, not illustrated. Rigid shell 616 includes a fill hole 630 into which a filling tube 632 is connected for allowing cavity 624 to be filled with deionized water in a manner similar to that described in conjunction with FIG. 4. In order to provide a pressure relief into which fluid displaced from cavity 624 can flow when membrane 622 is pushed inward by head 680, tube 632 is connected at the end remote from lens 610 to a reservoir illustrated as a cylindrical tank 640.

Antenna 650 is located at a distance away from lens 610 and head 680 and is oriented so as to direct RF&M energy illustrated as lines 614 towards lens 610. The separation between antenna 650 and lens 610 is not too important, so long as the antenna is located close enough to the surface of the lens in order to prevent spreading of the energy before it reaches the lens. While it might appear that significant phase shifts of the energy impinging on the surface of the lens should be avoided in order to prevent destructive interference at the focal point, in practice this is not important. Such destructive interference may take place at the focal point, but constructive interference will occur at a point which is no further from the focal point than one half wavelength ($\lambda/2$). Since the wavelength within the dielectric material is reduced by the square root of the dielectric constant, all the constructive interferences will be so close to the focal point that for practical purposes they may be considered to be at the focal point.

Antenna 650 is of a type suitable for hyperthermia purposes. Antenna 650 includes radiating arrangement 652 located under a conductive reflector 654. Radiating portion 652 of antenna 650 is fed from a source of microwaves (not illustrated) by way of a coaxial cable illustrated as 656 which passes through an aperture 658 in reflector 654.

Figure 7:
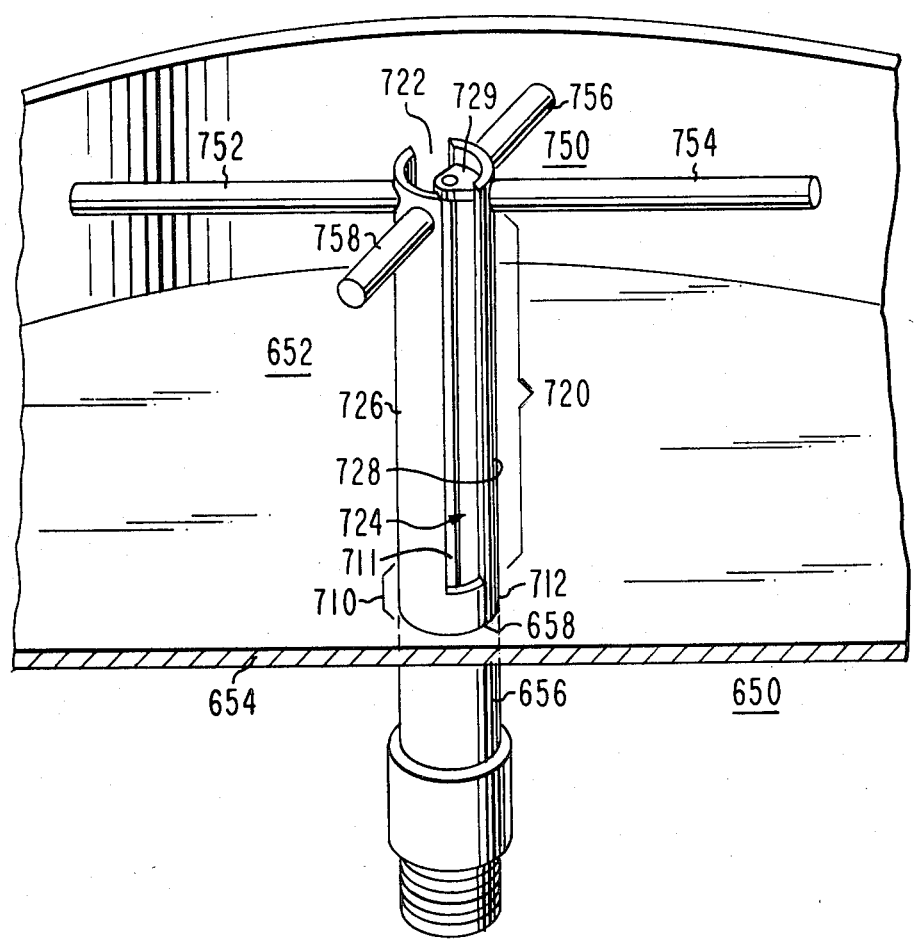
FIG. 7 illustrates details of an antenna used in the arrangement of FIG. 6.

FIG. 7 illustrates details of radiator 652. In FIG. 7, radiator 652 includes a short section 710 of coaxial transmission line (coax) which is an extension of a coaxial transmission line 656 forward of reflector 654. Connected to and extending from coaxial transmission line section 710 is a balun portion 720, and connected to balun portion 720 are individual radiators designated together as 750. Balun portion 720 is of well-known type and includes longitudinal slots 722 and 724 cut through a cylindrical conductor which is an extension of the outer conductor of coax 710, thereby leaving conductive portions 726 and 728. Slots 722 as known have a length of about one quarter wavelength ($\lambda/4$) at the frequency of operation. Center conductor 711 of coaxial transmission line section 710 extends into balun region 720 and intersects a shorting plate 729 which short-circuits the end of center conductor 711 to conductive section 728 in a plane in which antenna elements 750 lie. The set of antenna elements 750 includes a pair of long elements 752 and 754 which are mutually coaxial and which lie in the plane of shorting plate 729. One end of antenna element 752 is connected to the end of conductive portion 726, and an end of antenna element 754 is connected to the end of conductive portion 728. A second mutually coaxial pair of antenna elements 756 and 758 is oriented in the plane passing through shorting plate 729, and antenna elements 756 and 758 are also orthogonal to the axis of the pair of elements 752 and 754. One end of antenna element 756 is connected to the end of conductive portion 728, and one end of antenna element 758 is connected to the end of conductive portion 726. As known, such an antenna arrangement produces a circularly polarized field at the design center frequency. Such a circularly polarized field is particularly advantageous for hyperthermia treatment because the rotating electric field tends to produce at all points on the surface of the lens a component which approaches the surface of the lens at an angle which will be absorbed into the lens. Thus, a circularly polarized antenna tends to distribute energy into the lens more evenly than a linearly polarized antenna.

In an embodiment of the invention for use at 915 MHz, a lens of the form illustrated in FIG. 4 includes a hemispherical shell having a diameter of 11¾ inches (29.8 cm) of thermoplastic material having a wall thickness of 1/16 inch (1.58 mm). The bottom plate is a thermoplastic plate having a thickness of 3/16 inch (4.75 mm), defining a cavity which is filled with deionized water. The antenna is as illustrated in FIG. 7, and has a reflector diameter of 7⅞ inch (20.0 cm) and a reflector depth of 3¼ inch (8.25 cm). The length of the balun is 3¼ inch (8.25 cm), and the outer diameter of the coaxial transmission line is ½ inch (12.7 mm). The long radiators extend 2 3/16 inch (5.55 cm) from the outer edge of the balun conductive portions, and the short elements extend 1⅝ inch (4.13 cm). The antenna was located about one inch from the lens, and energized with 350 watts at 915 MHz. There was no cooling of the lens water. When applied to the thigh muscle of a dog, the temperature profile as a function of depth was as illustrated in FIG. 8.

Figure 8:
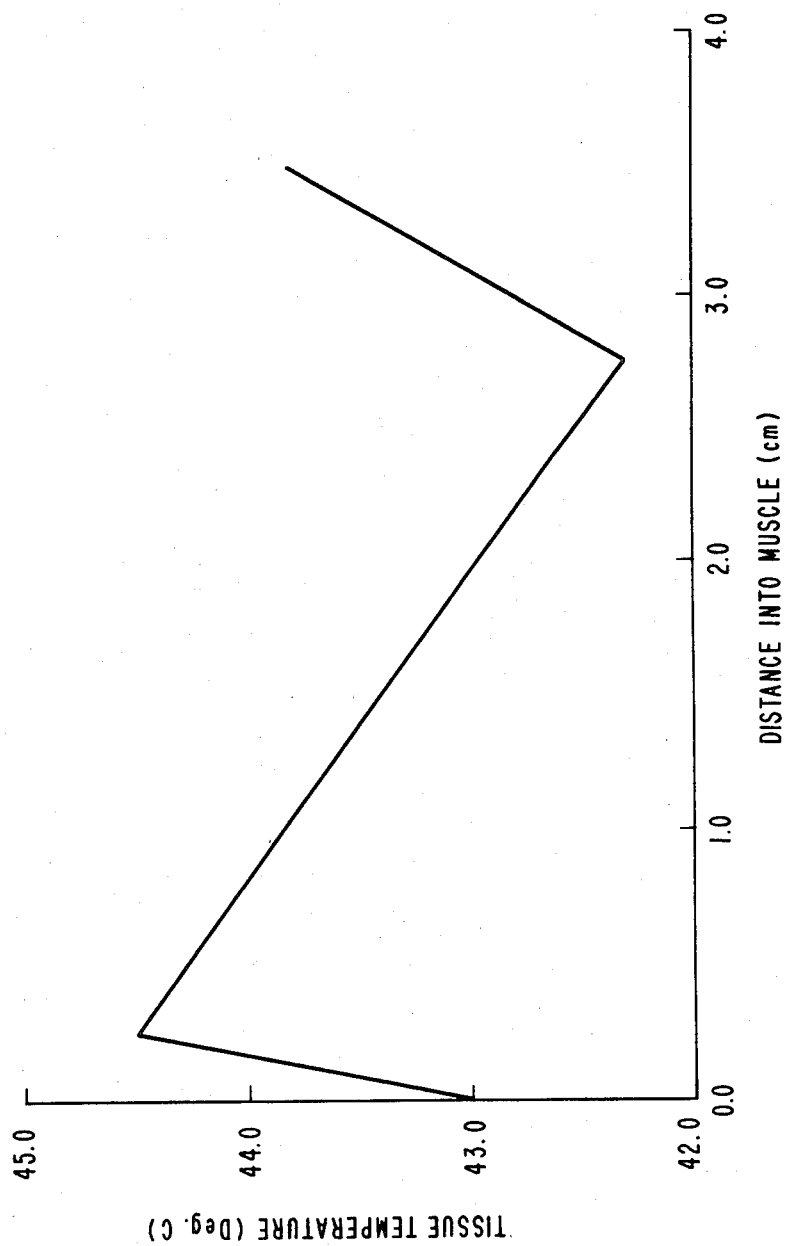
FIG. 8 is a plot of temperature as a function of depth in tissue under therapy by an apparatus including the lens of FIG. 4 with the antenna of FIG. 7.

In FIG. 8, the temperature of the surface (0.0 cm) of the muscle is relatively low (43.0° C.) because of cooling by heat conduction to the relatively cool lens. In the region from about 0.2 cm to 2.7 cm depth in the muscle, the temperature decreases because of attenuation of the signal and the resulting decreasing power density with increasing penetration. Beginning at a depth of penetration into the muscle of about 2.7 cm, the temperature begins to rise due to the focusing effect, so that the power density rises notwithstanding the attenuation of the signal by the overlying tissue. The temperature rises to about 43.8° C. at a depth of 3.5 cm. Data for greater depths was not measured.

Hyperthermia arrangements using a lens according to the invention are advantageous in part because of the reduced risk of exposure of therapists to focused microwave radiation. This reduced risk comes about because the energy approaching the flat surface from inside the lens is unfocused, and the focusing is only allowed to occur when the relatively high dielectric constant tissue of the patient is in contact with the surface of the lens. If a substantial air space is interposed between the patient or therapist and the lens, the focusing effect of the lens is negated. That is to say, in the absence of the high dielectric substance or material adjacent the flat surface of the lens, there is no focusing of energy, but rather there is a tendency toward total internal reflection of at least some of the energy, as described in conjunction with FIG. 3.

Figure 9B:
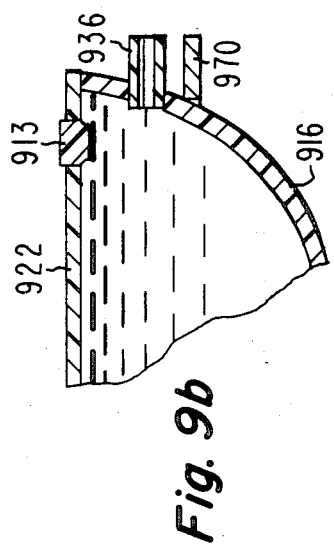
FIGS. 9a and b.
Figure 9A:
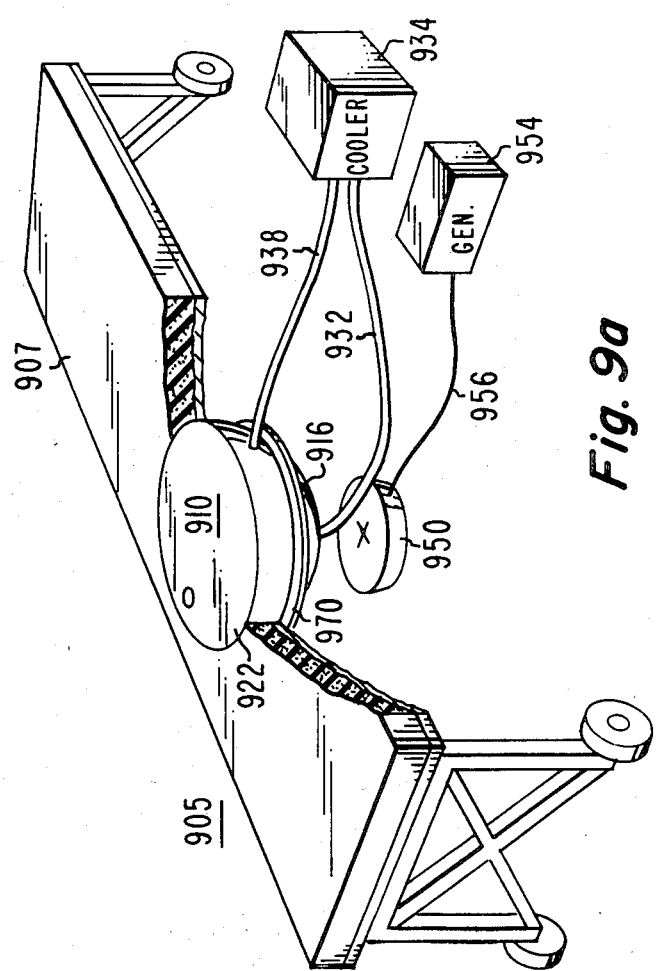

The arrangement of FIG. 9a illustrates a hyperthermia arrangement in which a bed designated generally as 910 is arranged with the flat surface of a lens according to the invention inserted into a hole in its upper (patient-facing) side 907. As illustrated in FIG. 9a and as also illustrated in cross-sectional detail in FIG. 9b, lens 910 includes a rigid top portion 922. Lens 910 also includes a fitting 936 for connection to a hot liquid return tube 938. Lens 910 is also connected to a cool liquid feed hose 932 which receives cool liquid from a cooler 934.

A rigid metal ring 970 having a inner diameter smaller than the maximum diameter of rigid domed shell 916 provides a surface by which lens 910 can be supported with the flat surface of plate 922 coincident with the plane of the top 907 of bed 905. The lens supporting structure is not illustrated. An antenna 950 is connected to a generator 954 by a coaxial cable 956. In use, lens 910 is filled with water, and bubbles are released through a hole which is then stopped with a stopper 913. The patient is placed on table 905 with the tumor to be treated located at the focal point of lens 910, and generator 954 is energized to produce a microwave field from antenna 950.

FIG. 10 illustrates an alternative arrangement in which top surface 1007 of bed 1005 is arranged with an annular notch or cutout 1080 for supporting lens 1010. The flat top surface of lens 1010 is a rigid disc 1084 formed from a rigid thermoplastic material. The lower portion 1086 of the shell defining lens cavity 1024 is a sheet of a resilient material rather than a rigid material. Filling of the cavity defined by plate 1084 and sheet 1086 is accomplished by means of a filling tube 1088 and synthetic rubber stopper 1089. Since lower sheet 1086 is resilient, it tends to be deformed into approximately semispheric shape by the weight of the water therein. Sheet 1086 is sealably held against rigid sheet 1084 by a metal ring 1090 held by screws (not illustrated).

FIGS. 11a and 11b illustrate top and bottom perspective views of a cylindrical lens, respectively, and FIG. 11c illustrates its use for hyperthermia treatment of an elongated limb. In FIG. 11, lens 1110 includes a rigid thermoplastic shell 1116 in the form of a portion of a right circular cylinder. Rigid flat thermoplastic end plates 1120 and 1122 are bonded to cylindrical shell 1116. Each of end plates 1120 and 1122 defines a semicircular cutout. Rectangular flat bottom plates 1124 and 1126 of rigid thermoplastic are bonded at their sides to edges of cylindrical shell 1116 and are also bonded to end plates 1120 and 1122. A rubber membrane 1130 is attached to the edges of bottom plates 1124 and 1126 and is folded over the ends of the lens and attached to the edges of the semicircular cutouts in end plates 1120 and 1122, thereby defining a closed cylindrical cavity.

In use, lens 1110 is filled with dielectric liquid and placed over the limb 1160 to be treated with the rubber membrane against the limb. As the lens is pressed over the limb, the limb is pushed against the rubber membrane and dielectric liquid is displaced. This displaced liquid is received by apparatus (not illustrated in FIG. 9). Microwaves are directed at the curved surface of the lens to provide an elongated heated area within the limb.

Other embodiments of the invention will be apparent to those skilled in the art. For example, there may be multiple fittings such as 530 around the periphery of a water-filled lens such as 510 to allow a more even distribution of cooled water across the lower surface of the lens. While the illustrated lenses are formed from or filled with a dielectric liquid, it is clear that similar lenses may be fabricated from solid dielectric materials. The rigid and/or the elastic portions of the shells may be loaded with discrete metal particles to form an artificial or metallic dielectric having a dielectric constant near the desired value, which has the effect of reducing reflections at the interface between the lens and the substance being heated. Instead of a single microwave frequency, the microwave power may be at a plurality of frequencies or distributed over a band of frequencies, whereupon the dielectric constant of the lens should be above about six over the band of significant frequencies. While the substance being heated has been described as having a dielectric constant equal to that of the lens, there is no need for identity; as the dielectric constants diverge, the power transfer decreases. In order to provide good heat transfer from the surface of tissues being treated and the lens liquid while keeping a relatively high dielectric constant, rigid discs 422 (FIG. 4) and 522 (FIG. 5) may be made from beryllium oxide ($B_eO$). It may be desirable before applying the RF&M energy to the patient by way of the lens to precool the surfaces of the tissue to be treated, which can be accomplished by passing cooled water through the lens, which is strapped to the patient. Since the spacing between the antenna and the lens in not important, it may be convenient to combine the antenna and the lens into a single assembly. While the cross-section of the lens has been described as defining a portion of a circle, the shape need only approximate a circle to the extent necessary for good focus; other curves such as sections of parabolas and the like approximate circles and may also be used.

What is claimed is:

1. An apparatus for focusing radio frequency or microwave electromagnetic energy within tissues being treated, comprising:
    a lens having, when operating, a cross-section substantially in the shape of a section of a circle, said lens comprising an enclosure defining a cavity and also comprising means for filling said cavity with a dielectric liquid having a dielectric constant greater than about 6, said enclosure including a horizontally oriented flat rigid base including a periphery, said base being adapted for being placed under and in contact with said tissues being treated, and a sheet of resilient material attached to said periphery and depending from said base, said sheet of resilient material being adapted to be deformed into approximately semispheric shape by said dielectric liquid; and
    a source of said radio frequency or microwave electromagnetic energy placed below and spaced away from said sheet of resilient material for directing energy upward toward said lens whereby said energy is focused on said tissues.

2. An apparatus according to claim 1 further comprising said dielectric liquid within said cavity, wherein said dielectric liquid is water.

3. An apparatus according to claim 2 wherein said water is deionized.

4. An apparatus according to claim 1 wherein said means for filling said cavity comprises an aperture adapted for transfer of fluid between the inside and the outside of said cavity, said aperture being located near that portion of said resilient sheet having the lowermost position when said cavity is filled.

5. An apparatus according to claim 1 further comprising a ring sealably holding said resilient sheet against said rigid base near said periphery.

* * * * *